United States Patent
Dakka et al.

(10) Patent No.: US 7,834,218 B2
(45) Date of Patent: *Nov. 16, 2010

(54) PROCESS FOR PRODUCING PHENOL AND METHYL ETHYL KETONE

(75) Inventors: Jihad M. Dakka, Whitehouse Station, NJ (US); Jon E. Stanat, Houston, TX (US); Francisco M. Benitez, Houston, TX (US); John S. Buchanan, Lambertville, NJ (US); Jane C. Cheng, Bridgewater, NJ (US); Jeffrey T. Elks, Geneva, IL (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/162,970

(22) PCT Filed: Feb. 8, 2007

(86) PCT No.: PCT/EP2007/001206

§ 371 (c)(1),
(2), (4) Date: Oct. 27, 2008

(87) PCT Pub. No.: WO2007/093358

PCT Pub. Date: Aug. 23, 2007

(65) Prior Publication Data

US 2009/0187047 A1  Jul. 23, 2009

(51) Int. Cl.
C07C 45/53 (2006.01)
C07C 37/08 (2006.01)
(52) U.S. Cl. .......................... 568/385; 568/768; 568/798
(58) Field of Classification Search .................. 568/385, 568/798; 585/461
See application file for complete search history.

(56) References Cited

U.S. PATENT DOCUMENTS

| 4,891,458 | A | | 1/1990 | Innes et al. ............... 585/323 |
| 4,992,606 | A | | 2/1991 | Kushnerick et al. ....... 525/467 |
| 5,059,736 | A | * | 10/1991 | Tamura et al. ............. 585/461 |
| 5,183,945 | A | * | 2/1993 | Stibrany et al. ............ 568/574 |
| 5,298,667 | A | * | 3/1994 | Iwanaga et al. ............ 568/385 |
| 5,371,310 | A | | 12/1994 | Bennett et al. ............. 585/467 |
| 5,557,024 | A | | 9/1996 | Cheng et al. ............... 585/467 |
| 5,922,920 | A | * | 7/1999 | Bond et al. ................. 568/342 |
| 2008/0086018 | A1 | | 4/2008 | Cheng et al. ............... 568/365 |

FOREIGN PATENT DOCUMENTS

DE 2300903 8/1973
EP 0 548 986 6/1993

OTHER PUBLICATIONS

Yen, "Phenool," *Process Economics Program Report No. 22B: Phenol Supplement B*, Stanford Research Institute, pp. 113-121, 261 and 263 (1977).

* cited by examiner

*Primary Examiner*—Sikarl A Witherspoon

(57) ABSTRACT

A process for producing phenol and methyl ethyl ketone comprises contacting benzene and a $C_4$ alkylating agent under alkylation conditions and in the presence of an alkylation catalyst comprising at least one molecular sieve of the MCM-22 family to produce an alkylation effluent comprising secbutylbenzene; wherein the contacting is conducted in a plurality of reaction zones and the C4 alkylating agent secbutylbenzene fraction is recovered from the alkylation effluent and comprises at least 95 wt % sec-butylbenzene, less than 100 wt ppm of $C_8+$ olefins, and less than 0.5 wt % of isobutylbenzene and tert-butylbenzene. The sec-butylbenzene fraction is then oxidized to produce sec-butylbenzene hydroperoxide and the hydroperoxide is cleaved to produce phenol and methyl ethyl ketene.

25 Claims, 1 Drawing Sheet

US 7,834,218 B2

PROCESS FOR PRODUCING PHENOL AND METHYL ETHYL KETONE

FIELD

The present invention relates to a process for co-producing phenol and methyl ethyl ketone.

BACKGROUND

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via gas/liquid extraction.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and co-produces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-421 and 261-263 of Process Economics Report No. 22B entitled "Phenol", published by the Stanford Research Institute in December 1977.

Sec-butylbenzene can be produced by alkylating benzene with n-butenes over an acid catalyst. The chemistry is very similar to ethylbenzene and cumene production. However, as the carbon number of the alkylating agent increases, the number of product isomers also increases. For example, ethylbenzene has one isomer, propylbenzene has two isomers (cumene and n-propylbenzene), and butylbenzene has four isomers (n-, iso-, sec-, and t-butylbenzene). For sec-butylbenzene production, it is important to minimize n-, iso-, t-butylbenzene, and phenylbutenes by-product formation. These by-products, especially iso-butylbenzene, have boiling points very close to sec-butylbenzene and hence are difficult to separate from sec-butylbenzene by distillation (see table below).

| Butylbenzene | Boiling Point, ° C. |
| --- | --- |
| t-Butylbenzene | 169 |
| i-Butylbenzene | 171 |
| s-Butylbenzene | 173 |
| n-Butylbenzene | 183 |

Moreover, iso-butylbenzene and tert-butylbenzene are known to be inhibitors to the oxidation of sec-butylbenzene to the corresponding hydroperoxide, a necessary next step for the production of methyl ethyl ketone and phenol. Thus, it is critical to maximize the sec-butylbenzene selectivity of the alkylation process.

Although by-products, such as isobutylbenzene and tert-butylbenzene, can be minimized by using a pure n-butene feed, for commercial production it is desirable to employ more economical butene feeds, such as Raffinate-2. A typical Raffinate-2 contains 0-1% butadiene and 0-5% isobutene. With this increased isobutene in the feed, a higher by-product make is expected, which further increases the importance of the sec-butylbenzene selectivity of the process.

In addition, it has now been found that the oxidation of sec-butylbenzene is also very sensitive to the presence of the higher ($C_8+$) olefins that tend to be produced as a result of the oligomerization reactions that compete with alkylation when butene is contacted with benzene in the presence of an acid catalyst. Moreover, certain of these butene oligomers, and in particular certain of the $C_{12}$ oligomers, have boiling points very close to sec-butylbenzene making them difficult to separate from alkylation effluent by distillation.

The present invention seeks to provide an optimized process for co-producing phenol and methyl ethyl ketone starting from benzene and a $C_4$ alkylating agent, such as Raffinate-2, and proceeding through an intermediate selective alkylation process for producing sec-butylbenzene.

U.S. Pat. No. 4,891,458 discloses a process for the alkylation of an aromatic hydrocarbon which comprises contacting a stoichiometric excess of the aromatic hydrocarbon with a $C_2$ to $C_4$ olefin under at least partial liquid phase conditions and in the presence of a catalyst comprising zeolite beta. In addition, it is known from, for example, U.S. Pat. No. 4,992,606 that MCM-22 is an effective catalyst for alkylation of aromatic compounds, such as benzene, with alkylating agents, such as olefins, having from 1 to 5 carbon atoms over a wide range of temperatures from about 0° C. to about 500° C., preferably from about 50° C. and about 250° C. Similar disclosures are contained in U.S. Pat. Nos. 5,371,310 and 5,557,024 but where the zeolites are MCM-49 and MCM-56 respectively.

In our International Application No. PCT/EP2005/008557, filed Aug. 5, 2005, we have described an integrated process for producing phenol and methyl ethyl ketone, the process comprising (a) contacting a feed comprising benzene and a $C_4$ alkylating agent under alkylation conditions with a catalyst comprising zeolite beta or an MCM-22 family zeolite to produce an alkylation effluent comprising sec-butylbenzene; (b) oxidizing the sec-butylbenzene to produce a hydroperoxide; and then (c) cleaving the hydroperoxide to produce phenol and methyl ethyl ketone. The $C_4$ alkylating agent can be a mixed butene feed, such as Raffinate-1 or Raffinate-2.

SUMMARY

In one aspect, the present invention resides in a process for producing phenol and methyl ethyl ketone, the process comprising:

(a) contacting benzene and a $C_4$ alkylating agent under alkylation conditions and in the presence of an alkylation catalyst comprising at least one molecular sieve of the MCM-22 family to produce an alkylation effluent comprising sec-butylbenzene; wherein the contacting is conducted in a plurality of reaction zones and said $C_4$ alkylating agent is supplied to each of said reaction zones (b) recovering a sec-butylbenzene fraction from said alkylation effluent, said fraction comprising at least 95 wt % sec-butylbenzene, less than 100 wt ppm of $C_8+$ olefins, and less than 0.5 wt % of isobutylbenzene and tert-butylbenzene;

(c) oxidizing the sec-butylbenzene recovered in (b) to produce a hydroperoxide; and (d) cleaving the hydroperoxide from (c) to produce phenol and methyl ethyl ketone.

Preferably, the fraction recovered in (b) comprises at least 97 wt % sec-butylbenzene, less than 50 wt ppm of $C_8+$ olefins, less than 0.1 wt % of isobutylbenzene and tert-butylbenzene.

In one embodiment, said sec-butylbenzene fraction is recovered directly from said alkylation effluent without prior chemical treatment of the effluent.

In another embodiment, said alkylation effluent is subjected to chemical treatment prior to recovery of said sec-butylbenzene fraction. Preferably, the chemical treatment comprises olefin oligomerization, selective reduction, selective oxidation, esterification, and the addition of heteroatoms to olefins, or a combination thereof.

Conveniently, the molecular sieve has an X-ray diffraction pattern including d-spacing maxima at 12.4±0.25, 6.9±0.15, 3.57±0.07 and 3.42±0.07 Angstrom. For example, the molecular sieve is selected from MCM-22, PSH-3, SSZ-25, ERB-1, ITQ-1, ITQ-2, MCM-36, MCM-49, MCM-56, UZM-8, and mixtures thereof. Preferably, the molecular sieve is selected from MCM-22, MCM-49, MCM-56 and isotypes thereof, and even more preferably from MCM-49, MCM-56 and isotypes thereof.

Preferably, the $C_4$ alkylating agent comprises a linear butene, for example 1-butene and/or 2-butene. In one embodiment, said linear butene is contained in a mixed $C_4$ stream such as a Raffinate-2 stream.

Conveniently, said alkylation conditions also include a temperature of from about 60° C. to about 260° C., a pressure of 7000 kPa or less, a feed weight hourly space velocity (WHSV) based on $C_4$ alkylating agent of from about 0.1 to 50 $hr^{-1}$, and molar ratio of benzene to butene of from about 1 to about 50, preferably of from about 2 to about 10, more preferably of from about 4 to about 9.

In one embodiment, said contacting (a) is conducted under at least partial liquid phase conditions.

In a separate embodiment, said alkylation effluent produced in (a) comprises polybutylbenzenes and the process further comprises contacting said polybutylbenzenes with benzene in the presence of a transalkylation catalyst to produce sec-butylbenzene. Conveniently, the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof.

Conveniently, the oxidizing (c) is conducted in the presence of a catalyst, such as a catalyst selected from (i) an oxo (hydroxo) bridged tetranuclear metal complex comprising manganese, (ii) an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof (iii) an N-hydroxy substituted cyclic imide either alone or in the presence of a free radical initiator, and (iv) N,N',N''-trihydroxyisocyanuric acid. In one embodiment, the oxidization catalyst is a heterogeneous catalyst.

Conveniently, the oxidizing (c) is conducted at a temperature of about 70° C. to about 200° C. and a pressure of about 0.5 to about 10 atmospheres (50 to 1000 kPa).

Conveniently, the cleaving (d) is conducted in the presence of a catalyst. The catalyst can be a homogeneous or heterogeneous catalyst. In one embodiment, the catalyst is a homogeneous catalyst, such as sulfuric acid.

Conveniently, the cleaving (d) is conducted at a temperature of about 40° C. to about 120° C., a pressure of about 100 to about 2500 kPa, and a liquid hourly space velocity (LHSV) based on the hydroperoxide of about 0.1 to about 100 $hr^{-1}$.

As used herein the term $C_8+$ olefin means any olefin containing 8 or more carbon atoms.

DETAILED DESCRIPTION OF THE EMBODIMENTS

Figure 2:
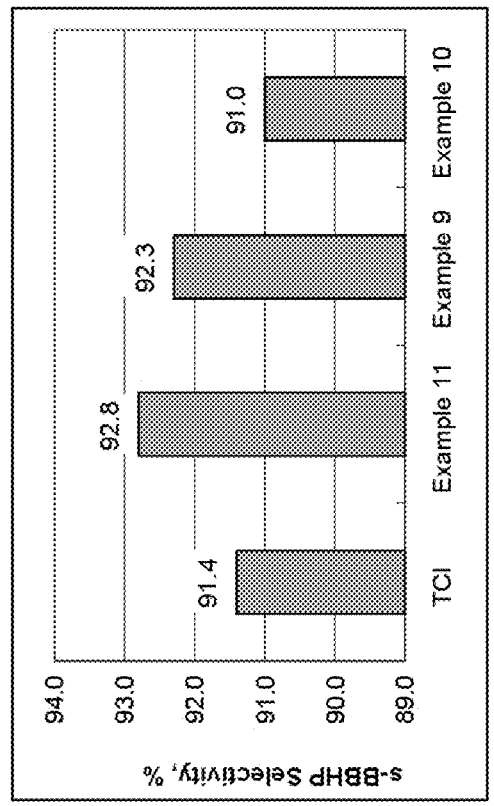
FIG. 2 compares the sec-butylbenzene hydroperoxide selectivity of the processes of Examples 9 to 11 with that of a comparative process using substantially pure sec-butylbenzene.

The present invention is directed to a process for producing sec-butylbenzene by alkylating benzene with a $C_4$ alkylating agent, such as a linear butene, and then converting the sec-butylbenzene recovered from the alkylation effluent to phenol and methyl ethyl ketone. The conversion involves initially oxidizing the sec-butylbenzene to produce the corresponding hydroperoxide and then cleaving the resulting hydroperoxide to produce the desired phenol and methyl ethyl ketone.

In particular, the invention is based on the discovery that the oxidation step to convert the sec-butylbenzene to the corresponding hydroperoxide is highly sensitive to presence of $C_8+$ olefins in the sec-butylbenzene fraction recovered from the alkylation effluent. Moreover, certain of these $C_8+$ olefins have boiling points very close to that of sec-butylbenzene and hence can not be readily separated from the sec-butylbenzene fraction by distillation. Thus the present invention seeks to obviate or reduce this problem by controlling the alkylation process or by chemically treating the sec-butylbenzene fraction so that the level of $C_8+$ olefins in the sec-butylbenzene fraction recovered from the alkylation effluent is less than 100 wt ppm and preferably less than 50 wt ppm.

Benzene Alkylation

The benzene employed in the alkylation step to produce sec-butylbenzene can be any commercially available benzene feed, but preferably the benzene has a purity level of at least 99 wt %, more preferably at least 99.8 wt %. Of the impurities typically found in a benzene feed, it is preferred to maintain the concentration of nitrogen compounds below 25 wt ppm, more preferably below 0.1 wt ppm and to maintain the concentration of sulfur compounds below 100 wt ppm, more preferably below 2 wt ppm. If necessary, nitrogen and sulfur levels can be reduced by clay treating or by passage through a molecular sieve or other sorption beds. Water levels in the benzene should also be maintained low, such as below 1000 wt ppm, preferably below 100 wt ppm. If necessary, water levels can be reduced by distillation or by passing the benzene through a molecular sieve drier.

The alkylating agent can be any aliphatic or aromatic organic compound having one or more available alkylating aliphatic groups capable of reaction with benzene and having 4 carbon atoms. Examples of suitable $C_4$ alkylating agents include monoolefins, such as linear butenes, particularly butene-1 and/or butene-2; alcohols (inclusive of monoalcohols, dialcohols, trialcohols, etc.) such as the butanols; dialkyl ethers, such as dibutyl ethers; and alkyl halides such as the butyl chlorides.

The alkylating agent can also be an olefinic $C_4$ hydrocarbon mixture such as can be obtained by steam cracking of ethane, propane, butane, LPG and light naphthas, catalytic cracking of naphthas and other refinery feedstocks and by conversion of oxygenates, such as methanol, to lower olefins.

For example, the following $C_4$ hydrocarbon mixtures are generally available in any refinery employing steam cracking to produce olefins: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table A below.

TABLE A

| Component | Crude $C_4$ stream | Raffinate 1 | | Raffinate 2 | |
|---|---|---|---|---|---|
| | | Solvent Extraction | Hydrogenation | Solvent Extraction | Hydrogenation |
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Isobutane | 0-1% | 0-1% | 0-1% | 0-2% | 0-2% |

Other refinery mixed $C_4$ streams, such as those obtained by catalytic cracking of naphthas and other refinery feedstocks, typically have the following composition:

| | |
|---|---|
| Propylene | 0-2 wt % |
| Propane | 0-2 wt % |
| Butadiene | 0-5 wt % |
| Butene-1 | 5-20 wt % |
| Butene-2 | 10-50 wt % |
| Isobutene | 5-25 wt % |
| Isobutane | 10-45 wt % |
| N-butane | 5-25 wt % |

$C_4$ hydrocarbon fractions obtained from the conversion of oxygenates, such as methanol, to lower olefins more typically have the following composition:

| | |
|---|---|
| Propylene | 0-1 wt % |
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N- + iso-butane | 0-10 wt % |

Any one or any mixture of the above $C_4$ hydrocarbon mixtures can be used in the process of the invention. In addition to linear butenes and butanes, these mixtures typically contain components, such as isobutene and butadiene, which can be deleterious to the process of the invention. For example, the normal alkylation product of isobutene with benzene is tert-butylbenzene which, as previously stated, acts as an inhibitor to the subsequent oxidation step. Thus, prior to the alkylation step, these mixtures preferably are subjected to butadiene removal and isobutene removal. For example, isobutene can be removed by selective dimerization or reaction with methanol to produce MTBE, whereas butadiene can be removed by extraction or selective hydrogenation to butene-1. Preferably, the alkylating agent employed in the process of the invention contains less than 5 mol %, more preferably less than 0.5 mol %, iso-butene and less than 0.5 mol %, more preferably less than 0.1 mol %, butadiene.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption. Typically the $C_4$ alkylating agent used in the present alkylation process contains less than 10 wt ppm, preferably less than 0.1 wt ppm, nitrogen, less than 100 wt ppm, preferably less than 3 wt ppm, sulfur and less than 1000 wt ppm, preferably less than 100 wt ppm, water.

Although not preferred, it is also possible to employ a mixture of a $C_4$ alkylating agent, as described above, and $C_3$ alkylating agent, such as propylene, as the alkylating agent in the alkylation step of the invention so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand of bisphenol-A production.

Conveniently, the total feed to the alkylation step of the present invention contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The alkylation catalyst used in the present process is preferably a molecular sieve of the MCM-22 family as catalyst. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

The molecular sieve of the MCM-22 family used in the present process is for example a crystalline molecular sieve having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

In one embodiment, the catalyst is unbound and has a crush strength much superior to that of catalysts formulated with binders. Such a catalyst is conveniently prepared by a vapor phase crystallization process, in particular a vapor phase crystallization process that prevents caustic (alkali metal hydroxides) used in the synthesis mixture from remaining in the zeolite crystals as vapor phase crystallization occurs.

The alkylation process is conducted such that the organic reactants, i.e., the alkylatable aromatic compound and the alkylating agent, are brought into contact with the alkylation catalyst in a suitable reaction zone such as, for example, in a flow reactor containing a fixed bed of the catalyst composition or in a catalytic distillation reactor, under effective alkylation conditions. Typically, the alkylation conditions include a temperature of from about 60° C. to about 260° C., for example between about 100° C. and about 200° C., a pressure of 7000 kPa or less, for example from about 1000 to about 3500 kPa, a weight hourly space velocity (WHSV) based on $C_4$ alkylating agent of between about 0.1 and about 50 $hr^{-1}$, for example between about 1 and about 10 $hr^{-1}$ and a molar ratio of benzene to alkylating agent of from about 1 to about 50, for example from about 2 to about 10, preferably from about 4 to about 9. Preferably, the alkylating agent is introduced to the reaction in stages, for example by providing the alkylation catalyst in a plurality of reaction zones connected in series and dividing the alkylating agent into a plurality of equal or different aliquot portions, each of which is fed to a different reaction zone. Most or all of the benzene is typically fed to the first reaction zone. Preferably, there are 4 or more reaction zones. Means of controlling reactor temperature include the staged injection of relatively cool alkylating agent, and the use of interstage heat exchangers.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen. Preferably, the reactants are at least partially in the liquid phase Using the catalyst and alkylation conditions described above, it is found that the alkylation step of the process of the invention is highly selective to sec-butylbenzene. In particular, it is found that the alkylation effluent generally comprises at least 93 wt %, preferably at least 95 wt %, sec-butylbenzene, less than 0.5 wt %, preferably less than 0.05 wt %, of isobutylbenzene, less than 0.1 wt %, preferably less than 0.05 wt %, of tert-butylbenzene and less than 150 wt ppm, such as less than 100 wt ppm, for example less than 50 wt ppm, preferably less than 30 wt ppm, of butene oligomers.

Although the alkylation step is highly selective towards sec-butylbenzene, the effluent from the alkylation reaction will normally contain some polyalkylated products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically effected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite. Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

Post Treatment of Sec-Butylbenzene

Sec-butylbenzene produced in the alkylation/transalkylation step is recovered, normally by distillation, and the resultant sec-butylbenzene fraction can be fed as-is to the subsequent oxidation step or can undergo post-treatment to reduce impurity levels before being fed to the oxidation step. The post-treatment can include further distillation although, as indicated above, iso-butylbenzene and tert-butylbenzene as well as certain butene oligomers, particularly the $C_{12}$ olefins, tend to boil at or near the same temperature as sec-butylbenzene and hence cannot be readily removed by distillation. It may therefore be desirable to subject the sec-butylbenzene fraction, either with or without initial distillation, to a chemical treatment process, to reduce the level of butene oligomers. Typically, the treated fraction fed to the oxidation unit should contain less than 100 wt ppm, preferably less than 50 wt ppm, more preferably less than 25 wt ppm, and most preferably less than 15 wt ppm, of $C_8$+ olefins, less than 0.5 wt %, preferably less than 0.1 wt %, of isobutylbenzene and tert-butylbenzene and at least 95 wt %, preferably at least 97 wt %, sec-butylbenzene.

One suitable chemical treatment to reduce the oligomer level in the alkylation effluent involves contacting the effluent with an acid, such as a mineral acid or a solid acid, at a temperature of about 0 to about 300° C. to convert the oligomers to alcohols or esters (e.g. ester of sulfuric acid)). After neutralization of the excess acid and, if necessary washing, drying, and distillation, the effluent can be fed to the oxidation step.

Another suitable chemical treatment to reduce the oligomer level in the alkylation effluent involves contacting the effluent with hydrogen in the presence of a catalyst, such as a noble metal, under conditions effective to saturate the oligomers. Suitable conditions include a temperature of about 0 to about 200° C., a pressure of about 100 to about 1000 kPa and a hydrogen to hydrocarbon mole ratio of about 0.001 to about 10.

A further suitable chemical treatment to reduce the oligomer level in the alkylation effluent involves etherification, in which the effluent is contacted with an alcohol, such as methanol, at a temperature of about 20 to about 300° C. and in the presence of a catalyst, such as an ion exchange resin.

A combination of the above treatment processes, such as combination of acid treatment and hydrogenation, can be used to reduce the level of butene oligomers in the alkylation effluent to the desired level.

Sec-Butyl Benzene Oxidation

In order to convert the sec-butylbenzene into phenol and methyl ethyl ketone, the sec-butylbenzene is initially oxidized to the corresponding hydroperoxide. This is accomplished by introducing an oxygen-containing gas, such as air, into a liquid phase containing the sec-butylbenzene. Unlike cumene, atmospheric air oxidation of sec-butylbenzene in the absence of a catalyst is very difficult to achieve. For example, at 110° C. and at atmospheric pressure, sec-butylbenzene is not oxidized appreciably, while cumene oxidizes very well under the same conditions. At higher temperature, the rate of atmospheric air oxidation of sec-butylbenzene improves; however, higher temperatures also produce significant levels of undesired by-products.

Improvements in the reaction rate and selectivity can be achieved by performing sec-butylbenzene oxidation in the presence of a catalyst. Suitable sec-butylbenzene catalysts include a water-soluble chelate compound in which multidentate ligands are coordinated to at least one metal from cobalt, nickel, manganese, copper, and iron. (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, preferably in an amount between 0.001 to 5 wt %, more preferably in an amount of no more than 2 wt % and even more preferably, in an amount of no more than 0.5 wt %, of the sec-butylbenzene.

Suitable conditions for the sec-butylbenzene oxidation step include a temperature between about 70° C. and about 200° C., such as about 90° C. to about 130° C., and a pressure of about 0.5 to about 10 atmospheres (50 to 1000 kPa). Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, preferably in the range of about 10 to 30%, to minimize the formation of byproducts.

A preferred reaction configuration is to use three to six reactor vessels, with the liquid cascading from one vessel to the next and with air introduced near the bottom of each vessel. Heat exchangers may be used to remove the heat of reaction. Preferably, the air leaving the reactor vessels is directed to one or more solid sorbent beds, which capture organics stripped out of the reaction vessels. These organics can be stripped from the sorbent beds and returned to the process. The sec-butylbenzene hydroperoxide produced may be concentrated, typically to a purity of 50 to 85 wt %, preferably using one or more evaporators or columns operating at subatmospheric pressure to remove unreacted sec-butylbenzene and other light components overhead.

Hydroperoxide Cleavage

The final reactive step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The crude MEK and crude phenol from the cleavage step may be subjected to further purification to produce purified MEK and phenol. A suitable purification process includes, but is not limited to, a series of distillation towers to separate MEK and phenol from other species. In a preferred arrangement, a crude MEK stream is taken overhead, and then subjected to further distillation to remove heavier and lighter components, to produce a finished MEK. The purified MEK is suitable for various further uses, e.g. as a solvent.

Phenol is also separated from heavier and lighter species. Preferably, heavy ends are cracked in a column with its bottom operated at a temperature in the range of about 270-370° C. A portion of a fraction rich in sec-butylbenzene, which is recovered during this purification process, may be discarded as a purge stream, to reduce the buildup of components such as tert-butylbenzene which boil close to sec-butylbenzene but which convert less readily in the oxidation step. The purified phenol is suitable for a variety of uses, including the production of caprolactam, of phenolic resins, and the manufacture of bisphenol-A, which can be used to make polycarbonates.

The following Examples are given for illustrative purposes and do not limit the scope of the invention.

Example 1

Comparative

Sec-butylbenzene Synthesis with MCM-22 and Single-Step Addition of 1-butene

A sample of fresh MCM-22 catalyst with a nominal composition of 80% zeolite and 20% Versal 300 alumina, extruded to 1/16 inch (1.6 mm) diameter cylinder form, was dried at 260° C. for a minimum of 2 hours before testing. 0.5 grams of catalyst (containing 0.4 grams of zeolite) was loaded between two 0.25-inch layers of inert, 8-grit quartz particles that had previously been dried at 121° C. until loaded into the stationary sample basket. 150 grams of reagent grade benzene was added to a 600-ml batch autoclave reactor. The sample basket assembly was installed in the autoclave reactor and sealed. The batch reactor was evacuated and purged twice with $N_2$ to ensure the elimination of air from the head space. The batch reactor was then pressured to about 200 psig (1480 kPa) with $N_2$ to ensure proper sealing and absence of leaks. Pressure was reduced to about 50 psig (446 kPa) and about 100 psig (791 kPa) of $N_2$ was used to quantitatively deliver 25 grams of reagent grade 1-butene from a transfer vessel into the batch reactor. The benzene to 1-butene ratio was 6:1 by weight and 4.3:1 by mole.

Reactor contents were mixed at 1000 rpm with a vertically positioned impeller located in the center of the stationary sample basket. The reactor was heated to 160° C. in about 20 minutes using a programmable autoclave controller to maintain constant ramp rate and temperature. After reaching temperature, the reactor pressure was increased to between 600 and 700 psig (4750–5540 kPa) by adding more $N_2$ to the system. Reaction time-zero was recorded from the point at which temperature and pressure targets (160° C., 600-700 psig) are attained and stable. The reaction period for this evaluation was 5 hours. Samples (1 cc each) were taken at 1-hour increments for GC analysis. At the end of the reaction period, the run was discontinued, the reactor cooled to ambient conditions and the total liquid product recovered for GC analysis.

Product analysis by GC was based on the assumption that composition of light components in the vapor phase was identical to those dissolved in liquid phase. The analysis was performed using an HP 6890 GC equipped with a DB-1 column (60 M, 0.25 mm ID, 1 micro liter film thickness) and an FID detector. A 0.2 micro liter portion of the product was injected onto the column and the following temperature program was used to perform the analysis: injection with 2-minute hold at −20° C., ramp at 8° C./min to 275° C., hold at 275° C. for 35 minutes. Response factors were used to convert GC area-based data to actual composition in the product. Butene conversion was determined by measuring unreacted butene relative to feed butene. Data obtained from the evaluation of Example 1 catalyst are reported in Table 1.

TABLE 1

MCM-22 with Single-Step Addition of 1-Butene in a Batch Reactor

| Hours on Stream | 1.0 | 2.0 | 3.0 | 4.0 | 5.0 |
|---|---|---|---|---|---|
| Feed Bz/C4 = Weight ratio | 6.0 | 6.0 | 6.0 | 6.0 | 6.0 |
| Feed Bz/C4 = Molar ratio | 4.3 | 4.3 | 4.3 | 4.3 | 4.3 |
| Butene Conversion, % | 72.4 | 83.7 | 90.9 | 94.9 | 97.1 |
| Product Selectivity, wt % | | | | | |
| i-Butane | 0.058 | 0.051 | 0.046 | 0.041 | 0.039 |
| n-Butane | 0.229 | 0.193 | 0.173 | 0.153 | 0.143 |
| $C_5$-$C_7$ | 0.169 | 0.139 | 0.132 | 0.124 | 0.135 |
| $C_8$= | 1.669 | 1.498 | 1.319 | 1.163 | 1.128 |
| $C_{9-11}$ | 0.131 | 0.096 | 0.076 | 0.086 | 0.079 |
| $C_{12}$ =+ $C_{10}$-$C_{11}$ Aromatics | 0.112 | 0.105 | 0.122 | 0.113 | 0.131 |
| $C_{13-5}$ | 0.063 | 0.066 | 0.065 | 0.093 | 0.082 |
| Cumene | 0.016 | 0.015 | 0.015 | 0.018 | 0.018 |
| t-Butylbenzene | 0.034 | 0.035 | 0.038 | 0.042 | 0.046 |
| i-Butylbenzene * | 0.000 | 0.000 | 0.000 | 0.000 | 0.000 |
| s-Butylbenzene | 90.113 | 90.703 | 91.050 | 91.089 | 91.279 |
| n-Butylbenzene | 0.011 | 0.015 | 0.013 | 0.015 | 0.014 |
| Di-butylbenzene | 7.012 | 6.591 | 6.459 | 6.636 | 6.526 |
| Tri-butylbenzene | 0.355 | 0.299 | 0.353 | 0.381 | 0.349 |
| Heavies | 0.028 | 0.194 | 0.138 | 0.045 | 0.031 |
| Sum | 100.0 | 100.0 | 100.0 | 100.0 | 100.0 |
| s-Butylbenzene (BB) Purity, % | | | | | |
| t-BB/all BB, % | 0.038 | 0.038 | 0.042 | 0.046 | 0.050 |
| i-BB */all BB, % | 0.000 | 0.000 | 0.000 | 0.000 | 0.000 |

TABLE 1-continued

| MCM-22 with Single-Step Addition of 1-Butene in a Batch Reactor | | | | | |
|---|---|---|---|---|---|
| s-BB/all BB, % | 99.950 | 99.945 | 99.944 | 99.937 | 99.935 |
| n-BB/all BB, % | 0.012 | 0.016 | 0.015 | 0.017 | 0.015 |
| Sum, % | 100.0 | 100.0 | 100.0 | 100.0 | 100.0 |
| Di-BB/s-BB Wt Ratio, % | 7.8 | 7.3 | 7.1 | 7.3 | 7.1 |

All samples collected at 160° C., 600-700 psig with 150 g of benzene and 25 g of 1-butene.
* i-Butylbenzene less than 0.5% in total butylbenzene not detectable with GC used.

Example 2

Comparative

Sec-Butylbenzene Synthesis Using MCM-49 with Single-Step Addition of 1-butene

The process of Example 1 was repeated but using a fresh MCM-49 catalyst with a nominal composition of 80% zeolite and 20% Versal 300 alumina, extruded to 1/16 inch cylinder form. Data are reported in Table 2.

TABLE 2

| MCM-49 with Single-Step Addition of 1-Butene in a Batch Reactor | | | | | |
|---|---|---|---|---|---|
| Hours on Stream | 1.0 | 2.0 | 3.0 | 4.0 | 5.0 |
| Feed Bz/C4= Weight ratio | 6.0 | 6.0 | 6.0 | 6.0 | 6.0 |
| Feed Bz/C4= Molar ratio | 4.3 | 4.3 | 4.3 | 4.3 | 4.3 |
| Butene Conversion, % | 70.8 | 82.2 | 89.0 | 93.2 | 95.3 |
| Product Selectivity, wt % | | | | | |
| i-Butane | 0.058 | 0.045 | 0.041 | 0.039 | 0.041 |
| n-Butane | 0.203 | 0.154 | 0.139 | 0.133 | 0.138 |
| $C_5$-$C_7$ | 0.187 | 0.146 | 0.130 | 0.115 | 0.128 |
| $C_8$= | 1.484 | 1.302 | 1.201 | 1.078 | 1.068 |
| $C_{9-11}$ | 0.117 | 0.112 | 0.094 | 0.089 | 0.086 |
| $C_{12}$=+ $C_{10}$-$C_{11}$ Aromatics | 0.115 | 0.112 | 0.100 | 0.103 | 0.114 |
| $C_{13-15}$ | 0.082 | 0.070 | 0.065 | 0.077 | 0.090 |
| Cumene | 0.011 | 0.012 | 0.014 | 0.015 | 0.017 |
| t-Butylbenzene | 0.036 | 0.036 | 0.038 | 0.041 | 0.043 |
| i-Butylbenzene * | 0.000 | 0.000 | 0.000 | 0.000 | 0.000 |
| s-Butylbenzene | 90.296 | 90.872 | 91.464 | 91.368 | 91.391 |
| n-Butylbenzene | 0.012 | 0.015 | 0.014 | 0.013 | 0.013 |
| Di-butylbenzene | 6.999 | 6.723 | 6.360 | 6.564 | 6.486 |
| Tri-butylbenzene | 0.368 | 0.354 | 0.314 | 0.340 | 0.356 |
| Heavies | 0.032 | 0.047 | 0.026 | 0.026 | 0.028 |
| Sum | 100.0 | 100.0 | 100.0 | 100.0 | 100.0 |
| s-Butylbenzene (BB) Purity, % | | | | | |
| t-BB/all BB, % | 0.040 | 0.040 | 0.041 | 0.045 | 0.047 |
| i-BB */all BB, % | 0.000 | 0.000 | 0.000 | 0.000 | 0.000 |
| s-BB/all BB, % | 99.947 | 99.944 | 99.943 | 99.941 | 99.938 |
| n-BB/all BB, % | 0.013 | 0.016 | 0.015 | 0.014 | 0.015 |
| Sum, % | 100.0 | 100.0 | 100.0 | 100.0 | 100.0 |
| Di-BB/s-BB Wt Ratio, % | 7.8 | 7.4 | 7.0 | 7.2 | 7.1 |

All samples collected at 160° C., 600-700 psig with 150 g of benzene and 25 g of 1-butene.
* i-Butylbenzene less than 0.5% in total butylbenzene not detectable with GC used.

Example 3

Sec-butylbenzene Synthesis with MCM-22 and Multi-Staged Addition of Equal Amounts of 1-butene A further 0.5 gram sample of the dried MCM-22 catalyst used in Example 1 was loaded between two 0.25-inch layers of inert, 8-grit quartz particles that were previously dried at 121° C. until loaded into the stationary sample basket. 150 grams of reagent grade benzene was added to a 600 ml batch autoclave reactor. The sample basket assembly was installed on the body of the autoclave reactor and sealed. The batch reactor was evacuated and purged twice with $N_2$ to ensure the elimination of air from the head space. The batch reactor was then pressured to about 200 psig (1480 kPa) with $N_2$ to ensure proper sealing and absence of leaks. Pressure was reduced to about 50 psig (446 kPa) and about 100 psig (791 kPa) of $N_2$ was used to quantitatively deliver 5 grams of reagent grade 1-butene from a transfer vessel into the batch reactor.

Reactor contents were mixed at 1000 rpm with a vertically positioned impeller located in the center of the stationary sample basket. The reactor was heated to 160° C. in about 20 minutes using a programmable autoclave controller to maintain constant ramp rate and temperature. After reaching temperature, the reactor pressure was increased to 600 and 700 psig (4750–5540 kPa) by adding more $N_2$ to the system. Reaction time zero was recorded from the point at which temperature and pressure targets (160° C., 600-700 psig) are attained and stable. At the end of 1-hour, a 1-cc sample was taken from the reactor. Another 5 grams of reagent grade 1-butene was quantitatively delivered from a transfer vessel into the batch reactor. This step-wise sampling and 5 gram 1-butene addition procedure was followed until a total of 5 increments (including the initial 5 gram charge) of 1-butene were added to the reactor. The final benzene to 1-butene ratio was 6:1 by weight and 4.3:1 by mole. The total reaction period for this evaluation was 5 hours. At the end of the reaction period, the run was discontinued, the reactor cooled to ambient conditions and the total liquid product recovered GC analysis. Incremental samples were also evaluated.

Product analysis by GC and data analysis were identical to those described in Example 1. Data obtained from the evaluation of Example 3 catalyst are reported in Table 3.

TABLE 3

| MCM-22 with Multi-Staged Addition of 1-Butene in a Batch Reactor | | | | | |
|---|---|---|---|---|---|
| Hours on Stream | 1.0 | 2.0 | 3.0 | 4.0 | 5.0 |
| Benzene Weight, g | 150 | 150 | 150 | 150 | 150 |
| Butene Weight, g | 5 | 10 | 15 | 20 | 25 |
| Feed Bz/C4= Weight Ratio | 30.0 | 15.0 | 10.0 | 7.5 | 6.0 |
| Feed Bz/C4= Molar Ratio | 21.5 | 10.7 | 7.2 | 5.4 | 4.3 |
| Butene Conversion, % | 94.7 | 95.5 | 95.9 | 95.8 | 96.6 |
| Product Selectivity, wt % | | | | | |
| i-Butane | 0.048 | 0.040 | 0.046 | 0.040 | 0.036 |
| n-Butane | 0.167 | 0.132 | 0.158 | 0.136 | 0.124 |
| $C_5$-$C_7$ | 0.442 | 0.233 | 0.204 | 0.141 | 0.109 |
| $C_8$= | 0.721 | 0.397 | 0.322 | 0.290 | 0.287 |
| $C_{9-11}$ | 0.035 | 0.015 | 0.025 | 0.037 | 0.028 |
| $C_{12}$=+ $C_{10}$-$C_{11}$ Aromatics | 0.069 | 0.038 | 0.033 | 0.035 | 0.042 |
| $C_{13-5}$ | 0.024 | 0.015 | 0.022 | 0.039 | 0.037 |
| Cumene | 0.157 | 0.064 | 0.023 | 0.016 | 0.012 |
| t-Butylbenzene | 0.064 | 0.063 | 0.061 | 0.059 | 0.057 |

TABLE 3-continued

MCM-22 with Multi-Staged Addition of 1-Butene in a Batch Reactor

| | | | | | |
|---|---|---|---|---|---|
| i-Butylbenzene * | 0.000 | 0.000 | 0.000 | 0.000 | 0.000 |
| s-Butylbenzene | 95.317 | 95.699 | 94.853 | 94.101 | 93.268 |
| n-Butylbenzene | 0.011 | 0.012 | 0.012 | 0.009 | 0.010 |
| Di-butylbenzene | 2.729 | 3.162 | 4.083 | 4.912 | 5.771 |
| Tri-butylbenzene | 0.183 | 0.121 | 0.131 | 0.172 | 0.197 |
| Heavies | 0.033 | 0.008 | 0.026 | 0.014 | 0.022 |
| Sum | 100.0 | 100.0 | 100.0 | 100.0 | 100.0 |
| s-Butylbenzene (BB) Purity, % | | | | | |
| t-BB/all BB, % | 0.068 | 0.066 | 0.064 | 0.063 | 0.061 |
| i-BB */all BB, % | 0.000 | 0.000 | 0.000 | 0.000 | 0.000 |
| s-BB/all BB, % | 99.921 | 99.921 | 99.923 | 99.928 | 99.929 |
| n-BB/all BB, % | 0.012 | 0.013 | 0.013 | 0.009 | 0.010 |
| Sum, % | 100.0 | 100.0 | 100.0 | 100.0 | 100.0 |
| Di-BB/s-BB Wt Ratio, % | 2.9 | 3.3 | 4.3 | 5.2 | 6.2 |

All samples collected at 160° C., 600-700 psig.
* i-Butylbenzene less than 0.5% in total butylbenzene not detectable with GC used.

Example 4

Sec-butylbenzene Synthesis with MCM-49 and Multi-Staged Addition of Equal Amounts of 1-butene The evaluation protocol of Example 3 was repeated but using the MCM-49 catalyst of Example 2. The results are summarized in Table 4.

TABLE 4

MCM-49 with Multi-Staged Addition of 1-Butene in a Batch Reactor

| | | | | | |
|---|---|---|---|---|---|
| Hours on Stream | 1.0 | 2.0 | 3.0 | 4.0 | 5.0 |
| Benzene Weight, g | 150 | 150 | 150 | 150 | 150 |
| Butene Weight, g | 5 | 10 | 15 | 20 | 25 |
| Feed Bz/C4= Weight Ratio | 30.0 | 15.0 | 10.0 | 7.5 | 6.0 |
| Feed Bz/C4= Molar Ratio | 21.5 | 10.7 | 7.2 | 5.4 | 4.3 |
| C4= Conv % | 92.9 | 94.4 | 94.9 | 95.1 | 96.8 |
| Product Selectivity, wt % | | | | | |
| i-Butane | 0.041 | 0.046 | 0.043 | 0.045 | 0.038 |
| n-Butane | 0.150 | 0.166 | 0.144 | 0.147 | 0.131 |
| $C_5$-$C_7$ | 0.485 | 0.258 | 0.164 | 0.120 | 0.105 |
| $C_8$= | 0.650 | 0.446 | 0.326 | 0.318 | 0.273 |
| $C_{9-11}$ | 0.045 | 0.046 | 0.042 | 0.030 | 0.034 |
| $C_{12}$=+ $C_{10}$-$C_{11}$ Aromatics | 0.043 | 0.046 | 0.042 | 0.036 | 0.036 |
| $C_{13-5}$ | 0.028 | 0.028 | 0.027 | 0.034 | 0.037 |
| Cumene | 0.024 | 0.018 | 0.012 | 0.008 | 0.008 |
| t-Butylbenzene | 0.068 | 0.062 | 0.063 | 0.061 | 0.058 |
| i-Butylbenzene * | 0.000 | 0.000 | 0.000 | 0.000 | 0.000 |
| s-Butylbenzene | 96.331 | 95.693 | 95.206 | 94.362 | 93.513 |
| n-Butylbenzene | 0.011 | 0.018 | 0.010 | 0.011 | 0.009 |
| Di-butylbenzene | 1.991 | 3.007 | 3.775 | 4.663 | 5.547 |
| Tri-butylbenzene | 0.115 | 0.148 | 0.124 | 0.151 | 0.184 |
| Heavies | 0.019 | 0.018 | 0.022 | 0.017 | 0.026 |
| Sum | 100.0 | 100.0 | 100.0 | 100.0 | 100.0 |
| s-Butylbenzene (BB) Purity, % | | | | | |
| t-BB/all BB, % | 0.071 | 0.065 | 0.066 | 0.064 | 0.062 |
| i-BB */all BB, % | 0.000 | 0.000 | 0.000 | 0.000 | 0.000 |
| s-BB/all BB, % | 99.918 | 99.917 | 99.923 | 99.925 | 99.928 |
| n-BB/all BB, % | 0.011 | 0.019 | 0.011 | 0.011 | 0.010 |
| Sum, % | 100.00 | 100.00 | 100.00 | 100.00 | 100.00 |
| Di-BB/s-BB Wt Ratio, % | 2.1 | 3.1 | 4.0 | 4.9 | 5.9 |

All samples collected at 160° C., 600-700 psig.
* i-Butylbenzene less than 0.5% in total butylbenzene not detectable with GC used.

Example 5

Sec-butylbenzene Synthesis with Jet-Milled MCM-49 and Multi-Staged Addition of Equal Amounts of 1-butene A sample of fresh MCM-49 was jet milled and then extruded with Versal 200 alumina into a 1/20 inch (1.3 mm) quadrulobe catalyst with a nominal composition of 60% zeolite and 40% alumina. 0.667 g of catalyst (containing 0.4 grams of zeolite) was loaded into the batch reactor and the evaluation protocol of Example 3 was repeated. Data are reported in Table 5.

TABLE 5

Jet-Milled MCM-49 with Multi-Staged Addition of 1-Butene in a Batch Reactor

| | | | | | |
|---|---|---|---|---|---|
| Hours on Stream | 1.0 | 2.0 | 3.0 | 4.0 | 5.0 |
| Benzene Weight, g | 150 | 150 | 150 | 150 | 150 |
| Butene Weight, g | 5 | 10 | 15 | 20 | 25 |
| Feed Bz/C4= Weight Ratio | 30.0 | 15.0 | 10.0 | 7.5 | 6.0 |
| Feed Bz/C4= Molar Ratio | 21.5 | 10.7 | 7.2 | 5.4 | 4.3 |
| Butene Conversion, % | 92.4 | 93.1 | 93.7 | 93.2 | 93.1 |
| Product Selectivity, wt % | | | | | |
| i-Butane | 0.051 | 0.044 | 0.038 | 0.040 | 0.037 |
| n-Butane | 0.197 | 0.157 | 0.136 | 0.145 | 0.134 |
| $C_5$-$C_7$ | 0.439 | 0.254 | 0.162 | 0.101 | 0.081 |
| $C_8$= | 0.751 | 0.325 | 0.261 | 0.251 | 0.247 |
| $C_{9-11}$ | 0.195 | 0.069 | 0.054 | 0.050 | 0.053 |
| $C_{12}$=+ $C_{10}$-$C_{11}$ Aromatics | 0.030 | 0.034 | 0.031 | 0.036 | 0.036 |
| $C_{13-15}$ | 0.022 | 0.028 | 0.024 | 0.030 | 0.035 |
| Cumene | 0.027 | 0.019 | 0.012 | 0.010 | 0.010 |
| t-Butylbenzene | 0.064 | 0.062 | 0.059 | 0.057 | 0.055 |
| i-Butylbenzene * | 0.000 | 0.000 | 0.000 | 0.000 | 0.000 |
| s-Butylbenzene | 95.479 | 95.827 | 95.428 | 94.937 | 94.432 |
| n-Butylbenzene | 0.016 | 0.015 | 0.013 | 0.012 | 0.012 |
| Di-butylbenzene | 2.294 | 2.914 | 3.621 | 4.159 | 4.681 |
| Tri-butylbenzene | 0.138 | 0.121 | 0.138 | 0.154 | 0.163 |
| Heavies | 0.297 | 0.130 | 0.024 | 0.017 | 0.024 |
| Sum | 100.0 | 100.0 | 100.0 | 100.0 | 100.0 |
| s-Butylbenzene (BB) Purity, % | | | | | |
| t-BB/all BB, % | 0.067 | 0.064 | 0.061 | 0.060 | 0.058 |
| i-BB */all BB, % | 0.000 | 0.000 | 0.000 | 0.000 | 0.000 |
| s-BB/all BB, % | 99.916 | 99.920 | 99.925 | 99.927 | 99.929 |
| n-BB/all BB, % | 0.016 | 0.015 | 0.014 | 0.013 | 0.013 |
| Sum, % | 100.0 | 100.0 | 100.0 | 100.0 | 100.0 |
| Di-BB/s-BB Wt Ratio, % | 2.4 | 3.0 | 3.8 | 4.4 | 5.0 |

All samples collected at 160° C., 600-700 psig.
* i-Butylbenzene less than 0.5% in total butylbenzene not detectable with GC used.

Example 6

Comparison of Batch Reactor Results

Table 6 compares batch reactor data of Examples 1 to 5 collected at 5 hours reaction time. When operated with a single-step addition of 1-butene, MCM-22 and MCM-49 catalysts produced sec-butylbenzene with 91% selectivity. When operated with multi-staged addition of 1-butene to reach the same final benzene/1-butene molar ratio of 4.3:1, MCM-22 and MCM-49 catalysts improved sec-butylbenzene selectivity to 93-94%. Multi-staged addition also provided a 3-fold reduction of butene oligomers, and a reduction of di-butylbenzenes and tri-butylbenzenes.

It is to be appreciated that at a 6:1 benzene/1-butene weight ratio (4.3 molar ratio), the 1-butene concentration is 14.3 wt % (1/7) if all of the feed 1-butene mixes with all of the feed benzene instantaneously upon addition. Given the relatively slow reaction rates and fast stirring, this is a reasonable approximation with a well-stirred autoclave reactor, and can be approached in a fixed bed reactor with adequate feed distribution nozzles at each feed injection level. The local concentrations would be higher with non-ideal mixing. For a fixed bed system, there will normally be two or more catalyst beds, preferably with a separate olefin feed injection zone upstream of at least two of these beds. Within each zone, there may be a single nozzle for introduction of olefins into the bulk flowing mixture, or preferably multiple nozzles.

TABLE 6

Comparison of Batch Reactor Results at the End of Run

| | Mode of Butene Addition | | | | |
|---|---|---|---|---|---|
| | Single-Step Addition | | Multi-Staged (5 × 5 g) Addition | | |
| Example | Example 1 | Example 2 | Example 3 | Example 4 | Example 5 |
| Catalyst | MCM-22 | MCM-49 | MCM-22 | MCM-49 | Jet-milled MCM-49 |
| Benzene (Bz) Weight, g | 150 | 150 | 150 | 150 | 150 |
| Total Butene ($C_4^=$) Weight, g | 25 | 25 | 5 × 5 | 5 × 5 | 5 × 5 |
| Total Feed Bz/C4 = Weight Ratio | 6.0 | 6.0 | 6.0 | 6.0 | 6.0 |
| Total Feed Bz/C4 = Molar Ratio | 4.3 | 4.3 | 4.3 | 4.3 | 4.3 |
| Butene Conversion, % | 97.1 | 95.3 | 96.6 | 96.8 | 93.1 |
| Product Selectivity, wt % | | | | | |
| i-Butane | 0.039 | 0.041 | 0.036 | 0.038 | 0.037 |
| n-Butane | 0.143 | 0.138 | 0.124 | 0.131 | 0.134 |
| $C_5$-$C_7$ | 0.135 | 0.128 | 0.109 | 0.105 | 0.081 |
| $C_8^=$ | 1.128 | 1.068 | 0.287 | 0.273 | 0.247 |
| $C_{9-11}$ | 0.079 | 0.086 | 0.028 | 0.034 | 0.053 |
| $C_{12}^=$ + $C_{10}$-$C_{11}$ Aromatics | 0.131 | 0.114 | 0.042 | 0.036 | 0.036 |
| $C_{13-5}$ | 0.082 | 0.090 | 0.037 | 0.037 | 0.035 |
| Cumene | 0.018 | 0.017 | 0.012 | 0.008 | 0.010 |
| t-Butylbenzene | 0.046 | 0.043 | 0.057 | 0.058 | 0.055 |
| i-Butylbenzene * | 0.000 | 0.000 | 0.000 | 0.000 | 0.000 |
| s-Butylbenzene | 91.279 | 91.391 | 93.268 | 93.513 | 94.432 |
| n-Butylbenzene | 0.014 | 0.013 | 0.010 | 0.009 | 0.012 |
| Di-butylbenzene | 6.526 | 6.486 | 5.771 | 5.547 | 4.681 |
| Tri-butylbenzene | 0.349 | 0.356 | 0.197 | 0.184 | 0.163 |
| Heavies | 0.031 | 0.028 | 0.022 | 0.026 | 0.024 |
| Sum | 100.0 | 100.0 | 100.0 | 100.0 | 100.0 |
| s-Butylbenzene (BB) Purity, % | | | | | |
| t-BB/all BB, % | 0.050 | 0.047 | 0.061 | 0.062 | 0.058 |
| i-BB */all BB, % | 0.000 | 0.000 | 0.000 | 0.000 | 0.000 |
| s-BB/all BB, % | 99.935 | 99.938 | 99.929 | 99.928 | 99.929 |
| n-BB/all BB, % | 0.015 | 0.015 | 0.010 | 0.010 | 0.013 |
| Sum, % | 100.00 | 100.00 | 100.00 | 100.00 | 100.00 |
| Di-BB/s-BB Wt Ratio, % | 7.1 | 7.1 | 6.2 | 5.9 | 5.0 |

All samples collected at 160° C., 600-700 psig, and 5 hours reaction time.
* i-Butylbenzene less than 0.5% in total butylbenzene not detectable with GC used.

When the same amount of butene was added stepwise (5-steps as in Examples 3-5) with nearly complete conversion of butene in between additions (92-97% butene conversion as in Examples 3-5), the maximum olefin concentration would be 2.9 wt % (20%×1/7). In a fixed bed reactor with essentially steady state operation, having multiple feed injection points is more or less the equivalent of multiple feed addition events to a batch reactor.

Example 7

Sec-butylbenzene Synthesis with Jet-Milled MCM-49 in Fixed-Bed Reactor at 3:1 Benzene/2-butene Molar Ratio 0.4 g of the jet-milled MCM-49 catalyst of Example 5 (but cut to 1/16 inch [1.6 mm] length) was used for alkylation of benzene with 2-butene in a fixed-bed reactor. The catalyst was diluted with sand to 3 cc and loaded into an isothermal, down-flow, fixed-bed, tubular reactor having an outside diameter of 4.76 mm (3/16"). The catalyst was dried at 150° C. and 1 atm with 100 cc/min flowing nitrogen for 2 hours. The nitrogen was turned off and benzene was fed to the reactor at 60 cc/hr until reactor pressure reached the desired 300 psig (2170 kPa). Benzene flow was then reduced to 7.63 cc/hr. 2-Butene feed (57.1% cis-butene, 37.8% trans-butene, 2.5% n-butane, 0.8% isobutene and 1-butene, and 1.8% others) was introduced from a syringe pump at 2.57 cc/hr. Feed benzene/butene molar ratio was maintained at 3:1 for the entire run. The reactor temperature was adjusted to 160° C. Liquid products were collected at reactor conditions of 160° C. and 300 psig (2170 kPa) in a cold-trap and analyzed off line. Butene conversion was determined by measuring unreacted butene relative to feed butene. Representative data are shown in Table 7.

Example 8

Sec-butylbenzene Synthesis with Jet-Milled MCM-49 in Fixed-Bed Reactor at 6:1 Benzene/2-butene Molar Ratio The process of Example 7 was repeated but using 0.6 g of the jet-milled MCM-49 catalyst of Example 5 (cut to 1/16 inch [1.6 mm] length) and with the feed benzene/butene molar ratio being maintained at 6:1 for the entire run (benzene at 11.47 cc/hr and butene at 1.93 cc/hour). Representative data are also shown in Table 7.

TABLE 7 sec-Butylbenzene Production with Jet-Milled MCM-49 in Fixed-bed Reactor

| Example | Example 7 | | Example 8 | |
|---|---|---|---|---|
| Feed Bz/C4 = Weight Ratio | 3:1 | | 6:1 | |
| Feed Bz/C4 = Molar Ratio | 4.2:1 | | 8.4:1 | |
| Days on Stream | 1.8 | 2.8 | 6.8 | 7.8 |
| Butene WHSV, $h^{-1}$ | 4.0 | 4.0 | 2.0 | 2.0 |
| Benzene WHSV, $h^{-1}$ | 16.7 | 16.7 | 16.7 | 16.7 |
| Butene Conversion, % | 96.30 | 95.41 | 97.41 | 97.33 |
| Product Selectivity, wt % | | | | |
| i-Butane | 0.003 | 0.003 | 0.000 | 0.000 |
| n-Butane | 0.000 | 0.000 | 0.000 | 0.000 |
| $C_5$-$C_7$ | 0.055 | 0.059 | 0.099 | 0.107 |
| $C_8$= | 0.443 | 0.865 | 0.466 | 0.474 |
| $C_{9-11}$ | 0.019 | 0.042 | 0.016 | 0.033 |
| $C_{12}$= + $C_{10}$-$C_{11}$ Aromatics | 0.157 | 0.135 | 0.066 | 0.073 |
| $C_{13-15}$ | 0.158 | 0.166 | 0.062 | 0.071 |
| Cumene | 0.243 | 0.251 | 0.156 | 0.159 |
| t-Butylbenzene | 0.093 | 0.078 | 0.078 | 0.068 |
| i-Butylbenzene * | 0.000 | 0.000 | 0.000 | 0.000 |
| s-Butylbenzene | 92.547 | 93.054 | 96.257 | 96.244 |
| n-Butylbenzene | 0.013 | 0.009 | 0.011 | 0.010 |
| Di-butylbenzene | 5.546 | 5.040 | 2.667 | 2.620 |
| Tri-butylbenzene | 0.405 | 0.287 | 0.113 | 0.125 |
| Heavies | 0.320 | 0.013 | 0.010 | 0.016 |
| Sum | 100.000 | 100.000 | 100.000 | 100.000 |
| s-Butylbenzene (BB) Purity, % | | | | |
| t-BB/all BB, % | 0.100 | 0.084 | 0.081 | 0.071 |
| i-BB */all BB, % | 0.000 | 0.000 | 0.000 | 0.000 |
| s-BB/all BB, % | 99.886 | 99.907 | 99.909 | 99.919 |
| n-BB/all BB, % | 0.014 | 0.009 | 0.011 | 0.011 |
| Sum, % | 100.00 | 100.00 | 100.00 | 100.00 |
| Di-BB/s-BB Wt Ratio, % | 6.0 | 5.4 | 2.8 | 2.7 |

All samples collected at 160° C. and 300 psig.
* iso-Butylbenzene less than 0.5% in total butylbenzene is not detectable with our GC.

When operated at 3:1 benzene/2-butene molar ratio (or 4.2:1 weight ratio), the 2-butene concentration is 18.9 wt % (1/5.3) if 2-butene mixes with benzene instantaneously. At this benzene/2-butene molar ratio, the MCM-49 catalyst produced sec-butylbenzene with 93% selectivity.

When operated at 6:1 benzene/2-butene molar ratio (or 8.4:1 weight ratio), the 2-butene concentration is 10.6 wt % (1/9.4) if 2-butene mixes with benzene instantaneously. At this benzene/2-butene molar ratio, the MCM-49 catalyst produced sec-butylbenzene with 96% selectivity. By-products such as butene oligomers and di-butylbenzenes and tri-butylbenzenes were reduced by about 50%. Thus reducing local concentration of butene in the fixed-bed reactor has a positive impact on sec-butylbenzene selectivity.

Example 9

Oxidation of Sec-Butylbenzene Produced in Batch Reactor by Multi-Staged Butene Addition at Total Benzene/Butene Molar Ratio of 4.3:1

The liquid products produced in Examples 3, 4, and 5 (batch reactor by multi-staged 1-butene addition) were combined. Benzene was removed under reduced pressure by a Roto-evaporator. Sec-butylbenzene was isolated by distillation under 50 mmHg vacuum using a 26-plate vacuum-jacked Older Shaw column with a reflux ratio of 10:1. Oxidation of sec-butylbenzene was carried out in a 100 cc Parr autoclave at 115° C. and 250-260 psig (1825–1894 kPa) nitrogen/oxygen (80/20) pressure. Into the 100 cc Parr autoclave was charged 0.185 g (1.1134 mmole) N-hydroxyphthalimide (NHPI) from Aldrich and 43.2 g (321.5 mmole) of the distilled sec-butylbenzene. The contents of the autoclave were pressurized to 220 psig (1618 kPa) with nitrogen followed by oxygen to an 80/20 molar ratio at room temperature. Next the mixture was heated to 115° C. with a mechanical stirring rate of 720 rpm. The temperature was maintained at 115° C. for 6 hours with frequent gas sampling of the head-space for nitrogen and oxygen. The oxygen content of approximately 20% was maintained throughout the heating period by replenishment from an oxygen PVT (pressure, volume, temperature) vessel.

At the completion of the run the liquid phase was analyzed by GC. Sec-butylbenzene conversion was 22.2 wt % and selectivity to sec-butylbenzene hydroperoxide was 92.3 wt %.

Example 10

Oxidation of Sec-Butylbenzene Produced in Fixed Bed Reactor at 3:1 Benzene/Butene Molar Ratio Liquid products produced in Example 7 (fixed-bed reactor at 3:1 benzene/butene molar ratio) were combined. The same procedure described in Example 9 was followed for sec-butylbenzene isolation and oxidation. Sec-butylbenzene conversion was 14.0 wt % and selectivity to sec-butylbenzene hydroperoxide was 91.0 wt %.

Example 11

Oxidation of Sec-Butylbenzene Produced in Fixed Bed Reactor at 6:1 Benzene/Butene Molar Ratio Liquid products produced in Example 8 (fixed-bed reactor at 6:1 benzene/butene molar ratio) were combined. The same procedure described in Example 9 was followed for sec-butylbenzene isolation and oxidation. Sec-butylbenzene conversion was 21.9 wt % and selectivity to sec-butylbenzene hydroperoxide was 92.8 wt %.

Example 12

Comparison of Sec-Butylbenzene Oxidation

Figure 1:
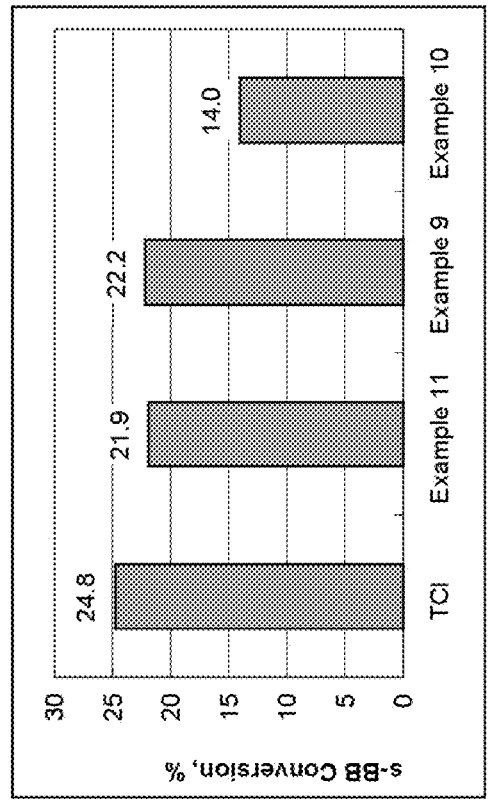
FIG. 1 compares the sec-butylbenzene conversion of the processes of Examples 9 to 11 with that of a comparative process using substantially pure sec-butylbenzene.

FIGS. 1 and 2 compare the sec-butylbenzene conversion and sec-butylbenzene hydroperoxide selectivity respectively of the processes of Examples 9 to 11 with that of comparative process using substantially pure sec-butylbenzene (having zero olefin impurities) as a bench-mark material.

FIG. 1 shows the improvement in sec-butylbenzene conversion with multi-staged addition of butene (Example 9 with 22.2% conversion) or with 6:1 benzene/butene molar ratio (Example 11 with 21.9% conversion), as compared with the 14% conversion obtained with the 3:1 benzene/butene molar ratio of Example 10. The highest conversion was, however, obtained with the pure sec-butylbenzene (24.8% conversion).

FIG. 2 shows the improvement in sec-butylbenzene hydroperoxide selectivity with multi-staged addition of butene (Example 9 with 92.3% selectivity) or with 6:1 benzene/butene molar ratio (Example 11 with 92.8% selectivity). These selectivities were higher than those obtained with the both 3:1 benzene/butene molar ratio of Example 10 (91% selectivity) and the pure feed (91.4% selectivity).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol and methyl ethyl ketone, the process comprising:
   (a) contacting benzene and a $C_4$ alkylating agent under alkylation conditions and in the presence of an alkylation catalyst comprising at least one molecular sieve of the MCM-22 family to produce an alkylation effluent comprising sec-butylbenzene; wherein the contacting is conducted in a plurality of reaction zones and said $C_4$ alkylating agent is supplied to each of said reaction zones;
   (b) recovering a sec-butylbenzene fraction from said alkylation effluent, said fraction comprising at least 95 wt% sec-butylbenzene, less than 100 wt ppm of C8+ olefins, and less than 0.5 wt% of isobutylbenzene and tert-butylbenzene;
   (c) oxidizing the sec-butylbenzene recovered in (b) to produce a hydroperoxide; and
   (d) cleaving the hydroperoxide from (c) to produce phenol and methyl ethyl ketone.

2. The process of claim 1, wherein the reactor temperature is controlled by means of staged injection of the $C_4$ alkylation agent wherein the $C_4$ alkylation agent is a relatively cool alkylating agent.

3. The process of claim 1, wherein said sec-butylbenzene fraction is recovered directly from said alkylation effluent without prior chemical treatment of the effluent.

4. The process of claim 1, wherein said alkylation effluent is subjected to chemical treatment prior to recovery of said sec-butylbenzene fraction.

5. The process of claim 1, wherein said alkylation effluent or said sec-butylbenzene fraction is chemically treated to reduce the level of butene oligomers.

6. The process of claim 5, wherein said chemical treatment is selected from hydrogenation, acid treatment, olefin oligomerization, selective reduction, selective oxidation, esterification, and the addition of heteroatoms to olefins, or a combination thereof.

7. The process of claim 1, wherein said molecular sieve of the MCM-22 family is selected from MCM-22, PSH-3, SSZ-25, ERB-1, ITQ-1, ITQ-2, MCM-36, MCM-49, MCM-56, UZM-8, and mixtures thereof.

8. The process of claim 1, wherein said molecular sieve is selected from MCM-22, MCM-49, MCM-56 and isotypes thereof.

9. The process of claim 1, wherein said molecular sieve is selected from MCM-49, MCM-56 and isotypes thereof.

10. The process of claim 1, wherein said chemical treatment is selected from hydrogenation and acid treatment or a combination thereof.

11. The process of claim 10, wherein said linear butene comprises 1-butene and/or 2-butene.

12. The process of claim 10, wherein said linear butene is contained in a mixed $C_4$ stream.

13. The process of claim 1, wherein said $C_4$ alkylating agent contains less than 5 mol % of iso-butene and less than 0.5 mol % of butadiene.

14. The process of claim 1, wherein said $C_4$ alkylating agent contains less than 0.5 mol % of iso-butene and less than 0.1 mol % of butadiene.

15. The process of claim 1, wherein said $C_4$ alkylating agent contains less than 10 wt ppm nitrogen, less than 100 wt ppm sulfur and less than 1000 wt ppm water.

16. The process of claim 1, wherein said $C_4$ alkylating agent contains less than 0.1 wt ppm nitrogen, less than 3 wt ppm sulfur and less than 100 wt ppm water.

17. The process of claim 1, wherein said alkylation conditions include a temperature of from about 60° C. to about 260° C., a pressure of 7000 kPa or less, a feed weight hourly space velocity (WHSV) based on $C_4$ alkylating agent of from about 0.1 to about 50 $hr^{-1}$ and a molar ratio of benzene to butene from about 1 to about 50.

18. The process of claim 17, wherein said molar ratio of benzene to butene is from about 4 to about 9.

19. The process of claim 1, wherein said contacting (a) is conducted under at least partial liquid phase conditions.

20. The process of claim 1, wherein said contacting also produces polybutylbenzenes and the process further comprises contacting said polybutylbenzenes with benzene in the presence of a transalkylation catalyst to produce sec-butylbenzene.

21. The process of claim 20, wherein the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof.

22. The process of claim 1, wherein said oxidizing (d) is conducted in the presence of a catalyst selected from:
(a) an oxo (hydroxo) bridged tetranuclear metal complex comprising manganese;
(b) an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof;
(c) an N-hydroxy substituted cyclic imide either alone or in the presence of a free radical initiator; and
(d) N, N', N"-trihydroxyisocyanuric acid either alone or in the presence of a free radical initiator.

23. The process of claim 1, wherein said oxidizing catalyst (d) is conducted in the presence of a catalyst comprising an N-hydroxy substituted cyclic imide either alone or in the presence of a free radical initiator.

24. The process of claim 1, wherein the cleaving (e) is conducted in the presence of a heterogeneous catalyst comprising a smectite clay.

25. The process of claim 1, wherein the cleaving (e) is conducted at a temperature of about 40° C. to about 120° C., a pressure of about 100 to about 1000 kPa, and a liquid hourly space velocity (LHSV) based on the hydroperoxide of about 1 to about 50 $hr^{-1}$.

* * * * *